United States Patent [19]

Harris

[11] 4,103,690
[45] Aug. 1, 1978

[54] SELF-SUTURING CARDIAC PACER LEAD

[75] Inventor: Donald Leal Harris, Miami Beach, Fla.

[73] Assignee: Cordis Corporation, Miami, Fla.

[21] Appl. No.: 779,686

[22] Filed: Mar. 21, 1977

[51] Int. Cl.² ............................................. A61N 1/04
[52] U.S. Cl. ............................... 128/418; 128/334 R; 128/340; 128/419 P; 227/83
[58] Field of Search ................ 128/404, 418, 419 P, 128/92 B, 92 ED, 334 R, 340, 215, 303 R; 227/66, 77, 82, 83, 85

[56] References Cited

U.S. PATENT DOCUMENTS

| 2,008,340 | 7/1935 | Salvati et al. | 128/215 |
| 3,516,412 | 6/1970 | Ackerman | 128/418 |
| 3,533,403 | 10/1970 | Woodson | 128/404 X |
| 3,754,555 | 8/1973 | Schmitt | 128/418 |
| 3,844,274 | 10/1974 | Nordstron | 128/303 R |
| 3,945,414 | 3/1976 | Gordon | 227/83 X |
| 4,057,067 | 11/1977 | Lajos | 128/418 |

FOREIGN PATENT DOCUMENTS 401,677 11/1933 United Kingdom ................ 128/334 R Primary Examiner—William E. Kamm
Attorney, Agent, or Firm—Kenway & Jenney

[57] ABSTRACT

The cardiac pacer lead disclosed herein may be secured or effectively sutured to cardiac tissue by ejecting a length of malleable wire through a tubular die having, at its distal end, a curved central bore which imparts a curvature of essentially predetermined radius to the wire. Passing through the tissue, the wire forms a circular loop or suture which can retain the lead in the desired position for stimulation.

6 Claims, 7 Drawing Figures

U.S. Patent  Aug. 1, 1978  4,103,690
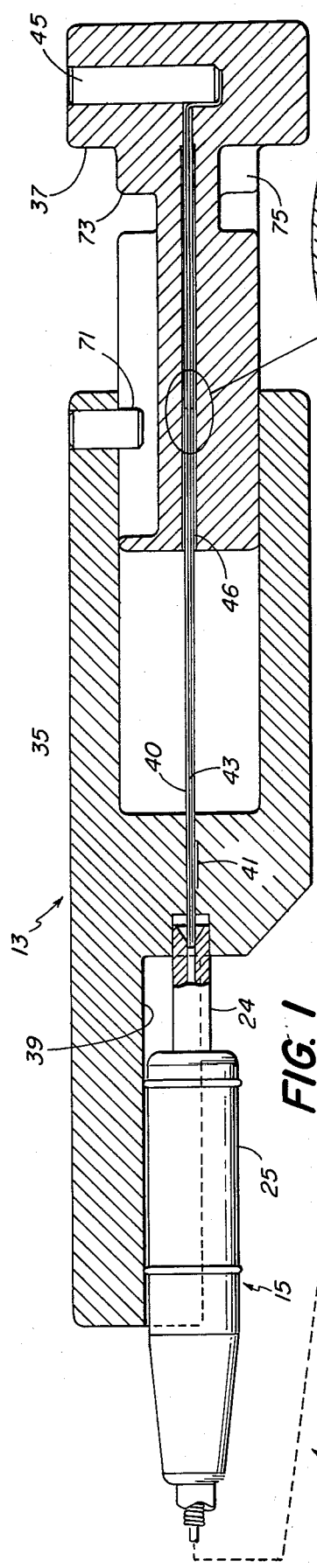
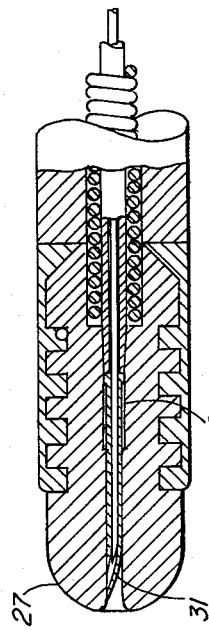
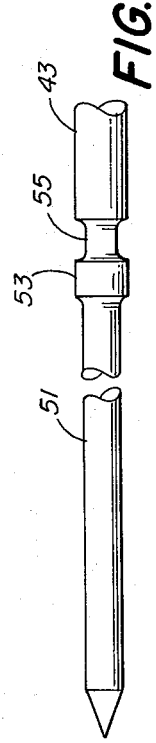
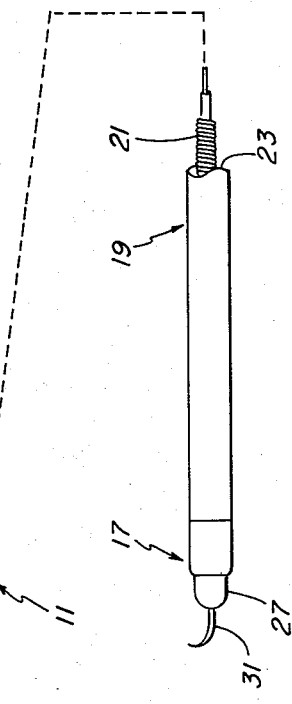
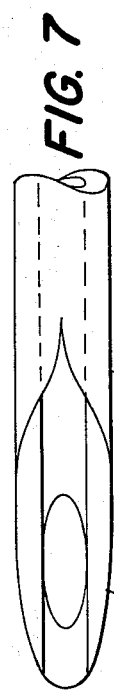
FIG. 1
FIG. 2
FIG. 3
FIG. 4
FIG. 5
FIG. 6
FIG. 7

SELF-SUTURING CARDIAC PACER LEAD

BACKGROUND OF THE INVENTION

The present invention relates to a self-attaching cardiac pacer lead and more particularly to such a lead which incorporates means for forming a wire suture which can secure the lead in position.

Various schemes have been proposed for retaining or securing, to heart tissue, the distal end of a flexible cardiac pacer lead. Such a flexible lead is typically employed because it is desirable to locate the pacer circuitry and batteries at a point remote from the heart in order to have more room and so as to facilitate replacement of the pacer upon depletion of its batteries. Some means, e.g., a flexible lead, is thus needed for providing conduction between the pacer's circuitry and the desired stimulation site. Further, some means is needed for securing the distal end of the lead to the desired location, e.g., atrium or ventricle. Among the schemes proposed previously may be noted the use of hooks or barbs; the use of a helical screw-in electrode; and the use of various clamping elements. Such constructions are shown, for example, in U.S. Pat. Nos. 3,416,533; 3,416,534; 3,472,234; 3,754,555; 3,814,104; 3,902,501; and 4,000,745.

While certain of these prior art constructions have met with limited success, there have likewise been certain problems and difficulties associated with different ones of these constructions. In some, the attachment device renders the tip of the lead bulky and increases the difficulty of initially positioning or inserting the lead, particularly where a pervenous approach is used. Particularly with regard to the hooked and barbed type of constructions, the attachment means may cause undue trauma to the heart, resulting in the formation of fibrosis which interferes with the electrical characteristics necessary for satisfactory stimulation. Thus, over time, an increased stimulation threshold is observed.

Among the several objects of the present invention may be noted the provision of a cardiac pacer lead which can be secured to cardiac tissue at the desired point of stimulation; the provision of such a lead which is relatively easily introduced by means of a pervenous approach; the provision of such a lead which, once attached, is relatively secure and yet which does not produce undue trauma to the cardiac tissue due to the means of attachment; the provision of such a pacer lead construction which is reliable and which is of relatively simple and inexpensive construction. Other objects and features will be in part apparent and in part pointed out hereinafter.

SUMMARY OF THE INVENTION

A cardiac lead in accordance with the present invention employs an electrical terminal for attachment to pacer circuitry and a tip for contacting cardiac tissue, there being a flexible conductor extending between the terminal and the tip. A fine, tubular die is mounted at the tip end of the lead, the die having a central bore which curves at its distal end thereby to impart a curvature of predetermined radius to a malleable wire driven through the die. The terminal, the tip, and the flexible conductor means are hollow to permit the passage therethrough of an elongate stylet for driving a length of wire through the die. Preferably, the length of wire is provided with means for limiting the extent of its passage through the die. Accordingly, the pacer lead tip may be secured to cardiac tissue by ejecting the wire through the die while the tip is in contact with the cardiac tissue. The wire thus passes through the tissue in a curved path which arches back towards the tip, effectively forming a suture for holding the tip in place.

BRIEF DESCRIPTION OF THE DRAWINGS

FIG. 1 is a side view, with parts broken away, of a self-suturing cardiac pacer lead in accordance with the present invention, together with a handle/stylet assembly which is assembled with the pacer lead at manufacture;

FIG. 2 is a sectional view to enlarged scale showing a portion of the coaxial stylet assembly which is used in actuating the suture-forming portion of the lead of FIG. 1;

FIG. 3 is a sectional view of the distal tip of the pacer lead of FIG. 1 showing, in a withdrawn position, a suture-forming die which is incorporated in the tip;

FIG. 4 is a view similar to FIG. 3 showing the die projecting from the tip and a suture formed;

FIG. 5 is a side view, to a still further enlarged scale, showing the suture-forming element or wire; and FIGS. 6 and 7 are side and top views, respectively, of the suture-forming die.

Corresponding reference characters indicate corresponding parts throughout the several views of the drawings.

DESCRIPTION OF THE PREFERRED EMBODIMENT

Referring now to FIG. 1, there is indicated at 11 a cardiac pacer lead in accordance with the present invention together with a handle/stylet assembly 13 which is preferably assembled with the lead at the time of original manufacture and stays with the lead until application of the lead to a patient's heart is essentially complete.

Except for the attaching means, the general construction of the lead 11 is essentially conventional and the lead comprises a terminal portion 15 connected to a distal tip portion 17 by a flexible conductor 19. In the preferred construction, the flexible conductor 19 comprises a loosely wound helical coil of Elgiloy wire 21, fitting loosely within a tube 23 of silicone rubber (Silastic). The terminal portion 15 of the lead comprises a tubular contact 24 to which the Elgiloy coil 21 is electrically connected, and a silicone rubber jacket 25. The particular form of terminal shown is adapted for use with cardiac pacers manufactured by the Cordis Corporation of Miami, Fla.

At its distal end, the helically coiled Elgiloy conductor 21 is connected to a metal tip or contact electrode 27. Electrode 27 is a conventionally shaped cylindrical electrode with its distal end rounded. It may also be terminated in a flat disk or in a concave contour. Contact tip 27 is molded to the silicone rubber tubing with silicone rubber as indicated at 29.

Except for the attaching means described hereinafter, the lead at FIG. 1 is of essentially conventional design for use with a pervenous approach to the heart. While the tip 27 would be solid in such prior constructions, the terminal 15 and the flexible conductor would be hollow to permit the insertion of a wire stylet. A stylet is used to stiffen the lead to facilitate its insertion through a suitable vein into the interior cavities of the patient's heart, the stylet being then removed after the lead was suitably positioned. In prior practice, the tip 27 was typically positioned at the apex of the patient's ventricle where it would rest under slight axial pressure from the lead itself until tissue would tend to grow in around the tip, giving it some security.

In accordance with the present invention, the electrode 27 is more positively secured to the cardiac tissue by means of a suture-like element which can be ejected from the electrode and simultaneously formed. For this purpose, the electrode 27 carries a needle-like die 31 which can project out in front of the electrode, through a central bore 32. During initial introduction of the lead, however, the die 31 is withdrawn into the electrode as shown in FIG. 3 so that the electrode presents a rounded leading edge facilitating its introduction along a vessel such as the patient's vein.

Rather than a solid stylet which is threaded through the lead only during the installation process, the operating apparatus of the present invention employs a coaxial construction comprising an outer, tubular stylet 40 and an inner stylet or central core 43. This coaxial construction is preferably assembled with the lead during original manufacture and is removed only after the lead has been secured to the patient's heart.

As may be seen in FIG. 1, the control device 13 comprises a handle portion 35 and an operating knob 37 which is axially slidable within the handle 35. Both of these pieces may be constructed of a suitably rigid plastic such as polycarbonate. The handle 35 also is formed with a recess 39 for loosely retaining the terminal portion 15 of the lead. In one construction of the embodiment illustrated, the outer portion 40 of the coaxial element comprised stainless steel hypodermic tubing of 0.016 inch outer diameter and 0.008 inch inner diameter. At its proximal end, this tube is rigidly attached to the handle 35. This attachment is facilitated by welding a small tab to the tubing 40 as indicated at 41. The distal end of the tubing 40 is tapered and is wedged or forced fit into a central bore 44 extending axially through the electrode 27. This may be seen in FIGS. 3 and 4. For reasons which will be apparent hereinafter, this is intended as a releaseable wedge fit.

Passing through the tubing 40 is the core wire 43. The proximal end of this wire extends through an axial bore in the knob 37 and is secured to the knob by means of a pin 45 driven radially into a transverse bore through the knob so as to clamp the wire. The tubing 40 also extends to the right of its point of attachment to the handle 35, so as to pass slidingly into the central axial bore in the knob element 37. Preferably, this bore is lined with a sleeve 46 which provides support for the tubing 40. Sleeve 46 may, for example, comprise a slightly larger size of hypodermic tubing, e.g., tubing having a 0.028 outer diameter and a 0.016 inch inner diameter. As will be understood, the knob member 37 is axially slidable with respect to the tubing 40 and is not secured thereto. The knob 37 thus provides a means for driving the central core 43 axially with respect to the tubing 40.

The distal end of the core 43 is shaped, as illustrated to enlarged scale in FIG. 5, so as to be formable into a suture. In keeping with the other dimensions given previously, the diameter of the core wire 43 over most of its length is about 0.007 inches diameter but the suture-forming tip portion 51 is ground down to a diameter of approximately 0.005 inch and given a sharp point, as illustrated. As will be understood, this ground down portion 51 itself constitutes a length of formable wire. A short section of the full diameter (0.007) of the core wire is left to form a collar 53 next to the suture-forming portion 51 and this in turn is followed by a necked-down section 55 of even smaller diameter, e.g., 0.004 inches. This necked-down section 55 provides a predetermined point of fracture, useful as described hereinafter.

As noted previously, the electrode tip 27 carries a needle-like tubular die 31. Prior to use and with the knob 37 in the right hand position as illustrated in FIG. 1, the die 31 is withdrawn wholly within the electrode tip 27 as illustrated in FIG. 3 so that the tip provides a rounded nose for the lead as it is being introduced through the patient's vascular system into his heart. The die is illustrated in greater detail and to enlarged scale in FIGS. 6 and 7. As may be seen in these figures, the central bore of the die curves upwardly at the distal (left hand) tip of the die whereas the proximal (right hand) end of the die comprises a collar 62 which limits the extend to which the die can be projected out through the front of the electrode 27, the central bore 32 within the electrode 27 being stepped as illustrated so as to engage this collar. The collar 62 is preferably formed by flaring the tubing and then grinding to achieve a diameter consistent with the diameter of the corresponding portion of the internal bore 32 within electrode 27.

The curved, forming portion 64 of the die 31 is conveniently formed by bending suitably-sized hypodermic tubing to the desired radius and then grinding off the curved portion in conformity with the original cylindrical surface. Consistent with the other dimensions given previously, a suitable size for the original hypodermic tubing forming the die is 0.012 inches outer diameter by 0.006 inches inner diameter. The radius of the curved tip of the die 31 is selected to produce the desired set to the suture wire, allowing for some slight spring back depending on the character of the suture wire. In the embodiment illustrated, a die formed with 0.050 inch radius curvature produces a circular suture of about 0.125 inch diameter, the suture material being half-hard Elgiloy.

During installation of the lead, the sequence of operations is essentially as follows. The lead and actuator assembly is delivered essentially in the posture illustrated in FIG. 1, i.e., the knob 37 is to the right so that the central core wire 43 is withdrawn and the needle-like die 31 is retracted within the electrode 27. The lead is introduced into the patient's vascular system in accordance with prior medical procedures and the electrode tip 27 at the distal end of the lead is worked into contact with a selected location on the patient's heart. During this operation, the coaxial assembly comprising the tube 40 and the core 43 act in the same manner as the solid stylet conventionally used in such procedures. A curve or set may be imparted to these elements just as with a conventional stylet for facilitating the guiding of the electrode during its passage through the patient's vascular system.

Once the electrode 27 at the distal end of the lead has been led to the selected stimulation site, the knob 37 can be driven to the left with respect to the handle portion 35 so as to drive the inner core 43 toward the tip. It should be understood that this force and movement of the core is with respect to the tubing 40 which guides and supports the core during this operation. As the suture-forming tip 51 of the core 43 moves to the left, as viewed in the drawings, it encounters and drives ahead of it the tubular die 31. Since the distal end of the die is sharp, it will pierce cardiac tissue before the force is great enough to cause the core wire to bend and form itself through the die.

The projection of the die 31 from the electrode 27 is limited by the engagement of the collar 62 with the corresponding shoulder on the interior bore in the electrode. Thus, when the die stops its motion to the left, further movement of the core will cause the tip portion 51 to pass through the die and the die will impart a predetermined curvature to this portion as it is ejected into the cardiac tissue. The length of the tip portion 51 is such that essentially a complete circle will be formed before the collar 53 comes to rest against the base of the die. At this point, the electrode tip 27 will be relatively securely attached to the cardiac tissue, the formed portion of the wire, in effect, constituting a suture holding the electrode in place. At this point, electrical testing can be conducted to determine if the stimulation site exhibits an appropriate threshold level of stimulation While the securing of the electrode tip 27 is essentially complete at this point, the process as thus far described is essentially reversible. That is, if it is desired to move the stimulation electrode, the knob 37 can be moved to the right, the suture tip 51 will be drawn back through the die, and the needle-like die will be pulled back into the electrode tip 27. Thus, the attachment can be released and, after re-positioning the electrode tip 27, the suture tip can be again ejected through the die so as to form a circular suture securing the electrode. In that the material of the suture tip 51 is to some extent malleable, i.e., capable of being formed by bending beyond its elastic limit, the number of times which the tip can be formed and unformed is, of course, finitely limited. However, at present, it is believed that even a substantial number of tries, e.g., 10, will not significantly weaken the suture material. Even the ability to make only a second try is believed to be highly advantageous, particularly when considering the security with which the attachment is made.

Once a satisfactory location and attachment is achieved, the knob 37 may be rotated several turns, the pin 71 being provided clearance in an annular groove 73. The formed suture tip 51 will not rotate since it is imbedded in the cardiac tissue and the resultant concentration of stress at the necked-down portion 55 will eventually cause it to fracture, thereby releasing the main portion of the core 43 from the completed suture tip. When the longitudinal groove 75 is brought up into alignment with pin 71, the knob 37 is moved slightly more forward. The resultant movement of the inner core 43, driving shoulder 53 against the flared portion of the die 31, will push the electrode tip 27 off the tubular stylet 40, separating the tapered wedge fit.

With these separations made, both the tubing 40 and the core 43 may be withdrawn from the lead so that the lead will then be in the highly desirable limp condition provided by the helically coiled wire 21. With the coaxial stylet withdrawn, the terminal 15 may be connected to a suitable pacer which is then implanted in conventional manner.

While the embodiment illustrated employs a suture-forming material of circular cross-section passing through a die with a circular bore and a curved tip, it should be understood that suture-forming elements of other cross-sections appropriate for accepting a predetermined curvature might also be used. For example, the suture-forming material might be relatively flat with its longer transverse axis perpendicular to the plane of the final suture. Such a material could be initially constrained in a conduit of conforming shape and a set could be imparted at the tip of the conduit by a wedge or pin which deflected the material beyond its elastic limit from its straight ahead course. Such an arrangement may be particularly useful where it is desired to form two circular sutures extending in opposite directions from the pacer lead tip.

In the embodiment illustrated, electrical contact is permitted between the electrode tip 27 and the die and suture material. Thus, the combined surface will operate to provide stimulation. As is known, however, an important parameter in determining the stimulation threshold is the current density, which is in turn a function of the effective electrode area. Thus, it may be advantageous in certain instances to electrically insulate the sutures from the electrode, e.g., by placing an insulating sleeve around the die. An alternative arrangement which also would provide a reduced contact area would be to eliminate the tip as an electrically active element and to apply the stimulating current through the suture alone.

As may be understood from the foregoing description, the present invention comprises as an important aspect the formation in situ of a suture which is created by axially ejecting an elongate suture-forming element through a die which deforms the material beyond its elastic limit so as to impart a predetermined curvature. The suture element will typically be initially straight though this is not absolutely required. For example, as the suture is withdrawn, e.g., incident to making a second try at electrode placement, the suture element will retain some residual set and not be returned to its initial straight state. It should be understood, however, that the presence or absence of some initial curvature is not significant in the practice of the present invention. Rather, it is the formation in situ of a suture by endwise movement of the material so that, as it is formed, it follows a predetermined path through the tissue. This may be contrasted with various devices in which elements spring out and take a preset shape of their own volition.

While the suture-forming technique employed in securing the pacer lead of the present invention has particular utility in that field, it should also be understood that this technique is also applicable to other medical environments since it offers the possibility of forming a closed loop suture at the point where it is needed. The suture so formed may, for example, be employed to join two tissue edges. The advantage, however, is that the sutures can be introduced by means of a tubular structure which is essentially of no larger diameter than a large hypodermic needle, e.g., one having the diameter of the die 31 or the tubing 40 employed in the construction illustrated.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:
1. A cardiac pacer lead comprising:
an electrical terminal;
a tip for contacting cardiac tissue;

flexible conductor means extending between said terminal and said tip;

a length of formable wire;

a tubular die mounted at the tip end of said lead, said die having a central bore which receives said formable wire, said die having, at the distal end thereof, means for deflecting said wire out of alignment with said bore to impart a curvature of predetermined radius to said wire as it is driven through the die, said length of wire being provided with means for limiting the passage of said wire through the die, said terminal, said tip and said flexible conductor means being hollow to permit the passage therethrough of elongate means for driving said wire through the die, said elongate means being operable from the terminal end of said lead, whereby said tip may be secured to cardiac tissue ejecting said length of wire through said die while said tip contacts cardiac tissue, the wire passing through the tissue in a curved path which arches back toward the tip effectively forming a suture holding the tip in place.

2. A cardiac pacer lead comprising:

an electrical terminal;

a tip for contacting cardiac tissue;

flexible conductor means extending between said terminal and said tip;

a tubular die mounted at the tip end of said lead, said die having a central bore which curves at the distal end of the die thereby to impart a curvature of predetermined radius to a wire driven through the die; and a length of wire in said bore, said length of wire being provided with means for limiting the passage of said wire through the die, said terminal, said tip and said flexible conductor means being hollow to permit the passage therethrough of elongate means ford driving said wire through the die, said elongate means being operable from the terminal end of said lead, whereby said tip may be secured to cardiac tissue ejecting said length of malleable wire through said die while said tip contacts said cardiac tissue, the wire passing through the tissue in a curved path which arches back toward the tip effectively forming a suture holding the tip in place.

3. A cardiac pacer lead as set forth in claim 2 wherein said tubular die is axially slidable in said tip to a limited extent between a retracted position and an extended position in which the die extends beyond the tip, said die being pointed to pierce tissue as it is driven to said extended position by a wire being advanced so as to be ejected through said die after said die reaches said extended position.

4. Surgical apparatus for forming a circular wire suture within normally inaccessible tissue, said apparatus comprising:

a formable wire element;

a needle-like tubular die member adapted for penetrating tissue, said die member having an inner bore shaped for closely guiding a wire element and having, at its distal end, means for deflecting a wire element out of alignment with said inner bore, the deflection taking the wire element beyond its elastic limit thereby to impart a curvature of essentially predetermined radius to the wire element; and a plunger sliding in said bore for driving said wire element through said bore and past said deflecting means thereby to eject said wire element along a path curving at essentially said predetermined radius, the length of said wire element being sufficient to form an essentially closed loop suture.

5. Cardiac pacer lead apparatus comprising:

an electrical terminal at the proximal end of the lead;

a tip at the distal end of the lead for contacting cardiac tissue;

a hollow, flexible conductor extending between said terminal and said tip;

a tubular die mounted within said tip of said lead, said die having a central bore which curves at the distal end of the die thereby to impart a curvature of predetermined radius to a wire driven through the die, said tubular die being axially slidable in said tip to a limited extent between a retracted position and an extended position in which the die extends beyond the tip, said die being pointed to pierce tissue as it is driven to said extended position;

a hollow stylet member extending through said hollow flexible conductor to said tip to which the stylet member is releasably attached;

extending through said stylet, a length of wire including a suture-forming portion which extends into said die, said suture-forming portion being provided with means for limiting the passage of said wire through the die; and means operable from the terminal end of said lead, for driving said wire with respect to said hollow stylet member whereby said tip may be secured to cardiac tissue ejecting said suture-forming portion through said die while said tip contacts said cardiac tissue, the wire passing through the tissue in a curved path which arches back toward the tip effectively forming a suture holding the tip in place.

6. Apparatus as set forth in claim 5 wherein said suture-forming portion is selectively severable from the remainder of said wire.

* * * * *